United States Patent
Lee et al.

(10) Patent No.: US 11,260,007 B2
(45) Date of Patent: Mar. 1, 2022

(54) COSMETIC COMPOSITION COMPRISING PARTICLES CONTAINING HIGH CONTENT OF CERAMIDE AND METHOD FOR PREPARING SAME

(71) Applicant: LG HOUSEHOLD & HEALTH CARE LTD., Seoul (KR)

(72) Inventors: Kyo Hoon Lee, Seoul (KR); Ei Suk Kim, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 16/963,038

(22) PCT Filed: Jan. 21, 2019

(86) PCT No.: PCT/KR2019/000827
§ 371 (c)(1),
(2) Date: Jul. 17, 2020

(87) PCT Pub. No.: WO2019/143206
PCT Pub. Date: Jul. 25, 2019

(65) Prior Publication Data
US 2020/0337969 A1      Oct. 29, 2020

(30) Foreign Application Priority Data

Jan. 19, 2018   (KR) .................. 10-2018-0007030

(51) Int. Cl.
*A61K 8/42*          (2006.01)
*A61K 8/06*          (2006.01)
(Continued)

(52) U.S. Cl.
CPC ............... *A61K 8/42* (2013.01); *A61K 8/062* (2013.01); *A61K 8/064* (2013.01); *A61K 8/41* (2013.01);
(Continued)

(58) Field of Classification Search
None
See application file for complete search history.

(56) References Cited

U.S. PATENT DOCUMENTS

| 6,372,236 | B1 | 4/2002 | Park et al. | |
| 2005/0152865 | A1* | 7/2005 | Yamamoto | A61Q 19/00 424/70.23 |
| 2014/0220139 | A1* | 8/2014 | Park | A61K 47/18 424/489 |

FOREIGN PATENT DOCUMENTS

| JP | 2002-302414 A | 10/2002 |
| JP | 2002-326920 A | 11/2002 |

(Continued)

OTHER PUBLICATIONS

Google Translate. English Translation of KR20140115853A. Obtained from https://patents.google.com/patent/KR20140115853A/en?oq=kr+20140115853 on Oct. 16, 2020. Originally published in Korean on Oct. 1, 2014, pp. 1-17. (Year: 2014).*

(Continued)

*Primary Examiner* — Isaac Shomer
(74) *Attorney, Agent, or Firm* — Birch, Stewart, Kolasch & Birch, LLP (57) ABSTRACT

In a cosmetic composition according to the present invention, a coating membrane with a multilayer lamella structure is formed on the outside of ceramide particles by using phytosphingosine, and therefore, the cosmetic composition is stably present without ceramide precipitation even in formulations with low viscosity as well as high viscosity although the particles contain a high content of ceramide, and a cosmetic composition showing an excellent skin barrier recovery effect can be provided.

11 Claims, 4 Drawing Sheets

(51) Int. Cl.
*A61K 8/41* (2006.01)
*A61K 8/92* (2006.01)
*A61Q 19/00* (2006.01)

(52) U.S. Cl.
CPC ............... *A61K 8/92* (2013.01); *A61K 8/922* (2013.01); *A61Q 19/007* (2013.01); *A61K 2800/412* (2013.01); *A61K 2800/652* (2013.01)

(56) References Cited

FOREIGN PATENT DOCUMENTS

| KR | 10-2005-0026778 | A |   | 3/2005 |   |
|----|-----------------|---|---|--------|---|
| KR | 10-0917302      | B1 |   | 9/2009 |   |
| KR | 10-2010-0011226 | A |   | 2/2010 |   |
| KR | 10-2014-0115853 | A |   | 10/2014 |   |
| KR | 20140115853     | A | * | 10/2014 |   |
| KR | 10-2017-0009408 | A |   | 1/2017 |   |
| KR | 10-2017-0090734 | A |   | 8/2017 |   |
| KR | 20170090734     | A | * | 8/2017 |   |
| WO | WO-2014020631   | A | * | 2/2014 | .......... B01F 11/0071 |

OTHER PUBLICATIONS

Barbora Školová, Andrej Kováčik, Ondřej Tesař, Lukáš Opálka, Kateřina Vávrová. "Phytosphingosine, sphingosine and dihydrosphingosine ceramides in model skin lipid membranes: permeability and biophysics." Biochimica et Biophysica Acta 1859 (2017) 824-834. (Year: 2017).*

Erol Yilmaz, Hans-Hubert Borchert. "Design of a phytosphingosine-containing, positively-charged nanoemulsion as a colloidal carrier system for dermal application of ceramides." European Journal of Pharmaceutics and Biopharmaceutics 60 (2005), pp. 91-98. (Year: 2005).*

Perry Romanowski. "Are ceramides good anti-agingingredients? Episode 77." https://thebeautybrains.com/2015/04/are-ceramides-good-anti-aging-ingredients-episode-77/ accessed Oct. 18, 2020, 33 printed pages. (Year: 2020).*

Yoshinori Masukawa, et al. "Characterization of overall ceramide species in human stratum corneum." Journal of Lipid Research, vol. 49, 2008, pp. 1466-1476. (Year: 2008).*

Simon M. Joscelyne, Gun Trägårdh. "Membrane emulsification—a literature review." Journal of Membrane Science 169 (2000) 107-117. (Year: 2000).*

TheLipidWeb. https://www.lipidmaps.org/resources/lipidweb/lipidweb_html/lipids/sphingo/lcb/index.htm accessed Aug. 2, 2021, 13 printed pages. (Year: 2021).*

Vyacheslav S. Bryantsev, Mamadou S. Diallo, and William A. Goddard, III. "pKa Calculations of Aliphatic Amines, Diamines, and Aminoamides via Density Functional Theory with a Poisson-Boltzmann Continuum Solvent Model." Journal of Physical Chemistry A, vol. 111, 2007, pp. 4422-4430. (Year: 2007).*

Arig Ibrahim-Hashim, Dominique Abrahams, Pedro M. Enriquez-Navas, Kim buddy, Robert A. Gatenby, Robert J. Gillies. "Tris-base buffer: a promising new inhibitor for cancer progression and metastasis." Cancer Medicine, vol. 6(7), 2017; pp. 1720-1729. (Year: 2017).*

Google Translate. English Translation of KR20170090734A. Accessed at https://patents.google.com/patent/KR20170090734A/en on Oct. 15, 2020, originally published in Korean on Aug. 8, 2017, pp. 1-15. (Year: 2017).*

International Search Report issued in PCT/KR2019/000827 (PCT/ISA/210), dated Apr. 26, 2019.

* cited by examiner

COSMETIC COMPOSITION COMPRISING PARTICLES CONTAINING HIGH CONTENT OF CERAMIDE AND METHOD FOR PREPARING SAME

TECHNICAL FIELD

The present invention relates to a cosmetic composition including particles containing a ceramide and phytosphingosine, and more specifically, to a cosmetic composition which contains a high content of ceramide by accommodating the ceramide in particles with a multi-layered lamellar structure using phytosphingosine but still exhibits excellent formulation stability and an excellent skin barrier recovery effect.

BACKGROUND ART

Intercorneocyte lipids, which are responsible for an important function in the permeability barrier of the skin, consist of ceramides, cholesterol, fatty acids, neutral lipids, and the like, and it is known that changes in these major ingredients affect the skin barrier function.

Among these ingredients, ceramides are major lipids constituting the lamellar structure of the intercorneocyte lipid and are well known to play an essential role in functioning as the permeability barrier of the skin. As skin aging progresses, the amount of ceramide is known to decrease, and accordingly, the skin barrier function is degraded, thereby reducing the amount of moisture in the skin, increasing moisture loss, delaminating the stratum corneum, and becoming a damaged or unhealthy skin barrier.

Such symptoms can be improved by supplying ceramides to the skin. However, since ceramides are poorly soluble substances and have structural specificity, it is difficult for a large amount of ceramide to be contained in a cosmetic. In the case of containing a large amount of ceramide in a cosmetic formulation, when ceramide particles are made small and used, stability in the formulation decreases, and thus a gelation phenomenon in which the ceramide is gelated by crystallization and precipitation occurs. As the particle size decreases, surface energy increases, and thus a high attractive force between particles is formed. Therefore, since the attractive force between ceramide particles increases, the ceramide is not completely dispersed in an oil-phase but precipitated in an aqueous phase, resulting in the occurrence of gelation due to bonding between ceramide particles. This phenomenon may be affected by the viscosity of a cosmetic formulation, and typically, as the viscosity is lower, the ceramide is usually more easily crystallized and thus precipitated. Therefore, when the ceramide is applied to an actual cosmetic formulation, there is a limitation in the content of ceramide which can be used in low-viscosity formulations such as a toner and a lotion.

In order to solve the problems, Patent Document 1 discloses a technique related to a ceramide on a nucleation agent using a solidified shell. According to this technique, stability is realized by removing fluidity with a solidified ceramide using a method in which granules formed by stabilizing an external ceramide are prepared, and then dispersed in an emulsion. However, this method has a disadvantage in that the content of actually used ceramide is decreased due to a large amount of an encapsulation agent used in the stabilization of an external ceramide, and the feeling of use which is important in the cosmetic composition is significantly degraded.

In addition, Patent Document 2 discloses a stabilization method by preparing a ceramide nanoliposome utilizing a high-pressure emulsification technique. This method has an advantage in that percutaneous absorption may increase, but as particles become smaller, the attractive force between particles increases, and, to stabilize a large amount of ceramide, an amount of a contained surfactant also needs to be increased in proportion to the ceramide amount. As a result, not only the feeling of use may be degraded, but also skin irritation may occur.

Therefore, there is still a need for a technique that can stabilize a cosmetic composition containing a high content of ceramide by overcoming the limitations of the prior art.

PRIOR-ART DOCUMENTS

Patent Documents (Patent Document 1) Korean Patent Application No. 2008-0072355
(Patent Document 2) Korean Patent Application No. 2003-0062910

DISCLOSURE

Technical Problem

The inventors of the present invention have conducted research to develop a cosmetic composition which solves the problem of the precipitation of a ceramide from ceramide particles in a composition containing a high content of ceramide and found a cosmetic composition which shows no precipitation of a ceramide even when containing a high content of ceramide and exhibits excellent formulation stability and an excellent skin barrier recovery effect by allowing ceramide-accommodating particles to have a multi-layered lamellar structure using phytosphingosine.

Therefore, the present invention is directed to providing a cosmetic composition which includes particles showing no precipitation of a ceramide in a formulation even when a high content of ceramide is contained in a membrane with a multi-layered lamellar structure and exhibits excellent formulation stability.

Technical Solution

One aspect of the present invention provides a cosmetic composition including particles containing a ceramide and phytosphingosine.

Hereinafter, the present invention will be described in detail.

The cosmetic composition of the present invention includes particles containing a ceramide and phytosphingosine.

The ceramide is a kind of sphingolipid in which a fatty acid is linked to sphingosine or phytosphingosine. The ceramide accounts for about 40% or more of the intercorneocyte lipid constituting the stratum corneum and is an essential ingredient for forming the structure of the stratum corneum or showing the function thereof. When cells are damaged by internal and external stress, the ceramide protects a subject from the stress by removing the damaged cells and also functions to prevent moisture loss and strengthen the skin barrier.

In the present invention, the ceramide may include both a natural ceramide and a pseudo-ceramide. The natural ceramide is a ceramide present in nature and may be a ceramide extracted from animals, plants, and microorganisms. The pseudo-ceramide is a generic term for compounds having a double-chain lamellar structure of the natural ceramide.

In the present invention, the lamellar structure prevents the gelation of the ceramide at an outer shell, and when the lamellar structure forms a macroemulsion that is surrounded by multiple lamellar layers consisting of two or more lamellar layers, it may contribute to the stabilization of the ceramide, and adequate viscosity and a light feeling of use may be realized.

In the present invention, the ceramide may be one or more selected from the group consisting of ceramide EOP, ceramide NS, ceramide NP, ceramide AS, ceramide EOS, ceramide NDS, ceramide AP, glucosylceramide, and omega-hydroxy ceramide, but the present invention is not limited thereto.

The ceramide may be included at 10 to 50 wt % per particle on average. For the ceramide which is a poorly soluble lipid ingredient to be stably present in an oil-in-water (O/W) formulation, the ceramide has to be present in an oil-phase ingredient. For this reason, it may be understood under the premise that the ceramide is uniformly accommodated in the particles that the content of ceramide included in the oil-phase ingredient means the content of ceramide accommodated in the particles. In the present invention, an average content of ceramide included in individual particles may range from 10 to 50 wt %, for example, 20 to 40 wt % or 25 to 35 wt %.

In addition, the ceramide may be included at 0.001 to 10 parts by weight with respect to 100 parts by weight of the entire composition and, for example, may be included at 0.01 to 7 parts by weight or 0.1 to 5 parts by weight.

Phytosphingosine is one of the ingredients of a ceramide constituting the skin barrier and may be obtained by extraction from natural yeast. Phytosphingosine is a synthetic sphingoid component, and sphingosine is a generic term for compounds such as sphingolipids, sphingoglycolipids, and sphingomyelin, has nitrogen, and is distributed in animal cell membranes and the like. Phytosphingosine helps to suppress the underlying skin hypersensitivity reaction by inhibiting the activity of causative bacteria of problematic skin, improve and gently care for the problematic skin. In addition, phytosphingosine is involved in improving tired skin due to aging by imparting elasticity to the skin and helps to enhance the function of the lipid layer of the skin and maintain a skin moisturizing effect. Additionally, phytosphingosine imparts a conditioning effect to the skin and hair and helps to manage vital skin and healthy hair.

In the present invention, the phytosphingosine may be included at 0.001 to 5 parts by weight with respect to 100 parts by weight of the entire composition and, for example, may be included at 0.01 to 3 parts by weight or 0.1 to 1 part by weight.

The particles according to the present invention may have a membrane with a multi-layered lamellar structure which is formed of phytosphingosine. The particles may be formed by agglomerating hydrophobic ingredients when hydrophobic ingredients such as a ceramide is mixed with hydrophilic ingredients. In the present invention, since phytosphingosine is further included as a hydrophobic ingredient, a coating membrane with a multi-layered lamellar structure is formed on the outer surface of the particles formed by agglomeration as described above, and thus it is possible to more stably accommodate a high content of ceramide. Since the membrane of the particle has a lamellar structure, even when a high content of ceramide is contained, the ceramide may not be precipitated out of the particle but may be stably maintained.

The particles may have a core-shell structure by containing a ceramide in a core and forming a membrane with a multi-layered lamellar structure on the outer surface of the particle.

As described above, since the particles have the outer coating membrane formed of phytosphingosine, even when a high content of ceramide is contained, a gelation phenomenon which is a conventional problem may be prevented.

In addition, in the present invention, the size of the particles may be a size that can be visually confirmed. In the present invention, the particles may have a size of 50 to 300 μm, for example, 100 to 300 μm or 150 to 300 μm. When the particles have a size within the above-described range, a high content of ceramide can be contained as desired in the present invention, and the ceramide does not precipitate even when the particles are crystallized, resulting in the prevention of a gelation phenomenon and achieving excellent formulation stability.

The particles may be prepared by a membrane emulsification method and, accordingly, may be prepared in a uniform size. When the size of the particles is less than 50 μm, a high content of ceramide may not be contained as desired in the present invention, and when the size of the particles is more than 300 μm, the ceramide in the particle is precipitated, and thus formulation stability is degraded.

The cosmetic composition according to the present invention may further include an oil-phase ingredient. The composition of the present invention may further include one or more oil-phase ingredients selected from the group consisting of cholesterol, a neutral lipid, a fatty acid, a fatty alcohol, an oil, and a wax. In the present invention, the oil-phase ingredient is included in the composition to help to form ceramide-accommodating particles.

In the present invention, the cholesterol is an ingredient that has been commonly used in the art for stabilizing the ceramide in the composition, and there is no particular limitation on a type thereof.

In the present invention, the neutral lipid may include squalane and/or a triglyceride having a C7 to C18 fatty acid, and the fatty acid may be one or more selected from the group consisting of C16 to C22 palmitic acid, stearic acid, and behenic acid. In addition, the fatty alcohol may be one or more selected from the group consisting of C16 to C22 cetyl alcohol, cetearyl alcohol, stearyl alcohol, and behenyl alcohol, but the present invention is not limited thereto.

As the oil and the wax, any of oils and waxes which are commonly used as ingredients of cosmetics in the art may be used. For example, the oil may be a silicone-based oil, an ester-based oil, a triglyceride-based oil, a hydrocarbon-based oil, or a vegetable oil, and, if necessary, these ingredients may be used in combination of one or more.

For example, as the silicone-based oil, a silicone-based fluid oil, a silicone-based crosspolymer dispersed in an oil, or the like may be used. For example, as the silicone-based fluid oil, cyclopentasiloxane, cyclohexasiloxane, cycloheptasiloxane, cyclomethicone, cyclophenylmethicone, cyclotetrasiloxane, cyclotrisiloxane, dimethicone, capryldimethicone, caprylyl trimethicone, caprylyl methicone, cetearyl methicone, hexadecyl methicone, hexyl methicone, lauryl methicone, myristyl methicone, phenyl methicone, stearyl methicone, stearyl dimethicone, trifluoropropyl methicone, cetyl dimethicone, diphenylsiloxyphenyl trimethicone, dimethylpolysiloxane, methylphenylpolysiloxane, decamethylcyclopentasiloxane, methyl trimethicone, or phenyl trimethicone may be used. The silicone-based oil ingredient may be used alone or in combination of two or more thereof. As the silicone-based crosspolymer, a dimethicone crosspolymer, a dimethicone/vinyl dimethicone crosspolymer, a dimethicone PEG-10/15 crosspolymer, or a PEG-12 dimethicone/PPG-20 crosspolymer may be used, but the present invention is not limited thereto.

As the ester-based oil, ascorbyl palmitate, ascorbyl linolate, ascorbyl stearate, diisostearyl malate, benzyl benzoate, benzyl laurate, butylene glycol dicaprylate/dicaprate, butylene glycol diisononanoate, butylene glycol laurate, butylene glycol stearate, butyl isostearate, cetearyl isononanoate, cetearyl nonanoate, cetyl caprylate, cetyl ethylhexanoate, cetyl isononanoate, ethylhexyl caprylate/caprate, ethylhexyl isononanoate, ethylhexyl isostearate, ethylhexyl laurate, hexyl laurate, octyldodecyl isostearate, isopropyl isostearate, isostearyl isononanoate, isostearyl isostearate, isocetyl ethylhexanoate, neopentyl glycol dicaprate, neopentyl glycol diethylhexanoate, neopentyl glycol diisononanoate, neopentyl glycol diisostearate, pentaerythrityl stearate, pentaerythrityl tetraethylhexanoate, dipentaerythrityl hexa acid esters, polyglyceryl-2 diisostearate, polyglyceryl-2 diisostearate, polyglyceryl-2 sesquiisostearate, polyglyceryl-2 isostearate, polyglyceryl-2 isostearate, polyglyceryl-2 tetraisostearate, polyglyceryl-2 triisostearate, polyglyceryl-3 diisostearate, polyglyceryl-3 isostearate, polyglyceryl-4 diisostearate, polyglyceryl-4 isostearate, polyglyceryl-6 diisostearate, polyglyceryl-6 sesquiisostearate, triethylhexanoin, or the like may be used.

As the triglyceride-based oil, C8-C12 acid triglycerides, C12-C18 acid triglycerides, caprylic/capric triglyceride, caprylic/capric/lauric triglyceride, C10-C40 isoalkyl acid triglycerides, C10-C18 triglycerides, glyceryl triacetylhydrostearate, soybean glyceride, tribehenin, tricaprine, triethylhexanoin, triheptanoin, triisostearin, tripalmitine, or tristearin may be used.

As the hydrocarbon-based oil, liquid paraffin (mineral oil), paraffin, Vaseline, microcrystalline wax, squalene, or the like may be used.

As the vegetable oil, avocado oil, wheat germ oil, rosehip oil, shea butter, almond oil, olive oil, macadamia oil, argan oil, meadowfoam oil, sunflower oil, castor oil, camellia oil, corn oil, safflower oil, soybean oil, canola oil, macadamia nut oil, jojoba oil, palm oil, palm kernel oil, or coconut oil may be used.

As the wax, any of waxes which are commonly used in cosmetics, such as a hydrocarbon-based wax, a vegetable wax, a silicone wax, or the like, may be used. For example, as the wax, candelilla wax, carnauba wax, rice wax, beeswax, lanolin, ozokerite, ceresin wax, paraffin wax, microcrystalline wax, C30-C45 alkyldimethylsilyl polypropylsilsesquioxane, or an ethylene/propylene copolymer or polyethylene wax may be used, but the present invention is not limited thereto.

The oil-phase ingredient is not particularly limited in a content thereof and may be included as the balance except for the above-described particles in the composition.

In the present invention, the membrane of the particle, which has a multi-layered lamellar structure, may be formed of one or more oil-phase ingredients selected from the group consisting of phytosphingosine, cholesterol, a neutral lipid, a fatty acid, a fatty alcohol, an oil, and a wax.

In addition, an active ingredient that exhibits efficacy as an oil-phase ingredient may be further included. For example, as the active ingredient, a lipophilic active ingredient such as retinol and vitamin E may be included.

The cosmetic composition according to the present invention may be a formulation having a viscosity of 0.1 to 40,000 cps. The ceramide tends to be easily crystallized in a low-viscosity composition and thus is easily precipitated. However, when phytosphingosine is further included as in the present invention, a coating membrane with a multi-layered lamellar structure is formed on the outer surface of ceramide particles, and thus stable particles in which ceramide is not precipitated may be prepared in a low-viscosity formulation as well as a high-viscosity formulation.

The cosmetic composition of the present invention may further include all kinds of ingredients that can be used in conventional cosmetics, such as a moisturizer, a thickener, a UV protection agent, a neutralizing agent, a fragrance, a preservative, an antioxidant, and a pigment.

The moisturizer may be hydrocarbons, oils and fats, hydrogenated oils, esters, fatty acids, lower alcohols, glycols, glycerol, higher alcohols, silicone oils, fluorine-based oils, lanolin derivatives, or plant sterol derivatives, but the present invention is not limited thereto. For example, the moisturizer may include one or more selected from the group consisting of glyceryl, butylene glycol, propylene glycol, dipropylene glycol, diglycerin, pentylene glycol, isoprene glycol, and erythritol.

The thickener is a polymer for adjusting viscosity and may be a polymer derived from plants, animals, or microorganisms or a synthetic polymer. For example, the thickener may be selected from the group consisting of an acrylate/C10-C30 alkyl acrylate crosspolymer, guar gum, xanthan gum, natto gum, ethyl cellulose, hydroxyethyl cellulose, carboxymethyl cellulose, sodium polyacrylate, glyceryl polyacrylate, and hydroxypropyl cellulose, but the present invention is not limited thereto.

The cosmetic composition according to the present invention may be prepared in any of formulations which are typically prepared in the art. For example, the cosmetic composition may be formulated as a toner such as a soft toner, a nutritional toner, or the like, a spray-type toner, a milky lotion such as a facial lotion, a body lotion, or the like, a cream such as a nourishing cream, a moisturizing cream, an eye cream, or the like, a stick, a skin serum, a cosmetic ointment, a spray, a gel, a pack, a sunscreen, a make-up base, a liquid-type or spray-type foundation, powder, a makeup remover such as a cleansing lotion or a cleansing oil, or a cleansing product such as a cleansing foam, a soap, a body cleanser, or the like, but the present invention is not limited thereto.

In an exemplary embodiment, the cosmetic composition is in an oil-in-water (O/W) or water-in-oil (W/O) formulation.

The cosmetic composition of the present invention may be used by a typical method of use, and the frequency of use may be varied depending on the skin condition or preference of a user.

Another aspect of the present invention provides a method of preparing a cosmetic composition, which includes preparing ceramide-accommodating particles by mixing an oil-phase part containing a ceramide and phytosphingosine with an aqueous phase part.

In the present invention, it may be understood that the aqueous phase part refers to a hydrophilic ingredient which can be mixed with water (purified water), and the oil-phase part refers to a hydrophobic ingredient which is not mixed with water (purified water).

The aqueous phase part may include ingredients for imparting viscosity to the composition. When viscosity is imparted to the composition by the ingredients, particles including a ceramide are uniformly dispersed in the preparation of the particles, and thus particles having excellent stability can be prepared. When particles are prepared while the composition is not imparted with viscosity, the particles are not uniformly dispersed but separated in an upper layer, resulting in a problem of particle stability such as agglomeration of particles. The oil-phase part may be included at 20 parts by weight or less, for example, 10 parts by weight or less, with respect to 100 parts by weight of the entire composition. When the content of the oil-phase part is within the above-described range, a macroemulsion which is desired in the present invention can be formed. When the content of the oil-phase part is 20 parts by weight or less, the particles formed by mixing the oil-phase part with the aqueous phase part may have a size of 50 to 100 μm, and when the content of the oil-phase part is 10 parts by weight or less, the particles may have a size of 100 to 300 μm. Accordingly, the particles containing a high content of ceramide which is desired in the present invention can be prepared. When the content of the oil-phase part is more than 20 parts by weight, an excessively large amount of particles are formed, and thus the particles may be broken due to physical stress during stirring, thereby reducing the size thereof. In this case, the size of the formed particle may be smaller than 50 μm.

In the present invention, a method of preparing ceramide-accommodating particles may use a typical membrane emulsification method. More specifically, the method may include producing an emulsion by dispersing an oil-phase part containing a ceramide and phytosphingosine in an aqueous phase part by permeating the oil-phase part through an emulsification membrane and converting the oil-phase part into a dispersed phase. In the present invention, since ceramide-containing particles are prepared by the membrane emulsification method without using ingredients that have been used to form particles, such as a nucleation agent or an encapsulation agent, a cosmetic composition which exhibits an excellent feeling of use when applied onto the skin can be prepared.

In an exemplary embodiment below, particles were prepared by dissolving each of an oil-phase part containing a ceramide and phytosphingosine and an aqueous phase part containing purified water while heating and permeating the oil-phase part through an emulsification membrane in the aqueous phase part. In this case, the emulsification membrane may have a pore size of 1 μm to 2 mm and may be porous alumina, porous zirconia, porous stainless, or porous glass.

In addition, according to the membrane emulsification, the oil-phase part containing a ceramide may permeate through an emulsification membrane at a pressure of 0.1 to 100 kPa, and accordingly, the size of particles may be adjusted. A cosmetic composition including particles including a ceramide may be prepared by cooling the solution in which particles are dispersed to 20 to 40° C.

The particles prepared as described above may contain a high content of ceramide and may be stably present in the composition for a long period of time.

The benefits and features of the present invention, and the methods of achieving the benefits and features will become apparent with reference to experimental examples and preparation examples to be described below. However, the present invention is not limited to the experimental examples and preparation examples to be disclosed below, and may be implemented in various other forms, and the experimental examples and preparation examples are provided for rendering the disclosure of the present invention complete and for fully conveying the scope of the invention to a person with ordinary skill in the technical field to which the present invention pertain.

Advantageous Effects

According to a cosmetic composition of the present invention, since a coating membrane with a multi-layered lamellar structure is formed on the outer surface of ceramide particles using phytosphingosine, the particles can be stably present without precipitation of ceramide in a low-viscosity formulation as well as a high-viscosity formulation even though the particles have a high content of ceramide, and accordingly, a cosmetic composition exhibiting an excellent skin barrier recovery effect can be provided.

DESCRIPTION OF DRAWINGS

FIG. 1 is a set of photographs of particles prepared according to the present invention as observed through a microscope (left: optical microscope, right: polarized microscope), wherein FIG. 1A shows particles with a composition of Comparative Example 1, FIG. 1B shows particles with a composition of Comparative Example 2, and FIG. 1C shows particles with a composition of Example 1.

FIG. 2 is a set of photographs of particles prepared according to the present invention as observed through an electron microscope after storage at room temperature for 4 weeks, wherein FIG. 2A shows particles with a composition of Comparative Example 1, FIG. 2B shows particles with a composition of Comparative Example 2, and FIG. 2C shows particles with a composition of Example 1.

MODES OF THE INVENTION

Hereinafter, the present invention will be described in detail with reference to the following examples. However, it should be understood that the following examples and experimental examples proposed herein are given for the purpose of illustration only and are not intended to limit the scope of the present invention.

Example 1 and Comparative Examples 1 and 2.
Preparation of Cosmetic Composition

Cosmetic compositions were prepared in compositions shown in Table 1 below. Specifically, a cosmetic composition of Example 1 was prepared as follows. First, an aqueous phase part was introduced into a continuous phase tank with temperature control and stirring functions and dissolved while being heated at 40 to 60° C., and then stirring was performed at 50 to 500 rpm. In addition, an oil-phase part containing a ceramide was introduced into a dispersed phase tank and dissolved while being heated at 50 to 90° C., and then membrane emulsification was performed while applying a pressure of 0.1 to 100 kPa, thereby preparing ceramide particles. A cosmetic composition including the prepared ceramide particles was cooled to 30° C., thereby finally preparing a cosmetic composition including particles with a lipid membrane structure.

Compositions of Comparative Examples 1 and 2 were prepared in the same manner as in Example 1 except that both a ceramide and phytosphingosine were not contained in an oil-phase part and phytosphingosine was not contained in an oil-phase part, respectively.

TABLE 1

| | Ingredient (parts by weight) | Example 1 | Comparative Example 1 | Comparative Example 2 |
|---|---|---|---|---|
| Aqueous phase part | Purified water | 78.8 | 78.8 | 79.1 |
| | Acrylate/C10-30 alkyl acrylate crosspolymer | 0.2 | 0.2 | 0.2 |
| | Glycerin | 5 | 5 | 5 |
| | Dipropylene glycol | 5 | 5 | 5 |
| | 1,2-Hexanediol | 2 | 2 | 2 |
| Oil-phase part | Caprylic/capric triglyceride | 1.2 | 3 | 1.2 |
| | Behenic acid | 2 | 3 | 2 |
| | Behenyl alcohol | 1 | 3 | 1 |
| | Cholesterol | 1.5 | — | 1.5 |
| | Phytosphingosine | 0.3 | — | — |
| | Ceramide NP | 3 | — | 3 |
| | Total | 100 | 100 | 100 |

Experimental Example 1. Confirmation of Characteristic of Ceramide Particle

1) Confirmation of Particle Form

The ceramide particles prepared in Example 1 were observed using an optical microscope and a polarized microscope. FIG. 1A shows particles with a composition of Comparative Example 1 which does not contain a ceramide, FIG. 1B shows particles with a composition of Comparative Example 2 which contains typically used lipids to stabilize a ceramide, and FIG. 1C shows particles with a composition of Example 1 which further contains phytosphingosine.

Figure 1:
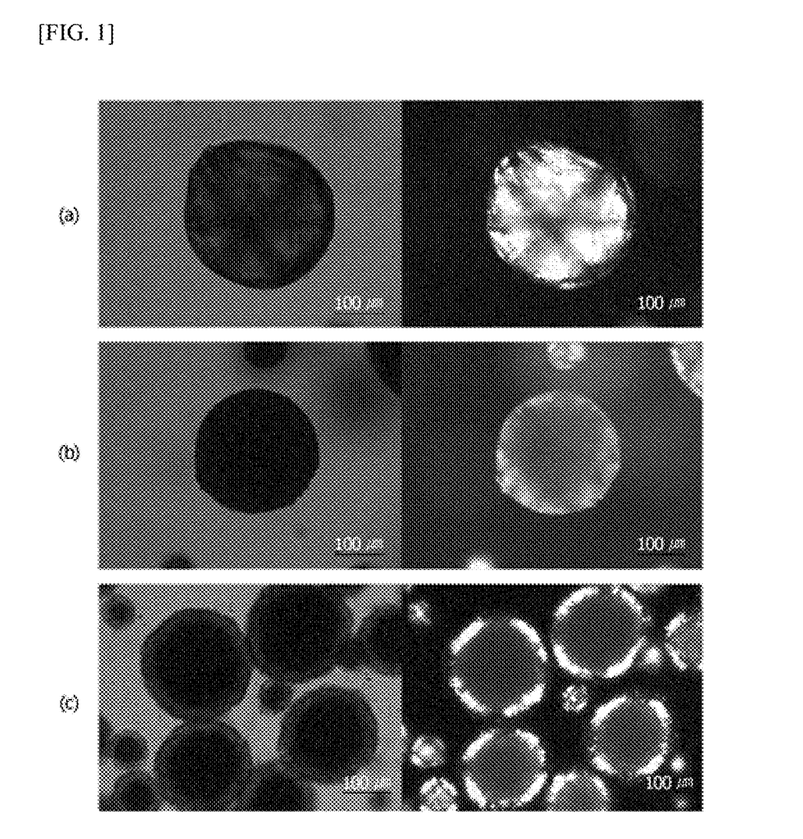
Figure 2:
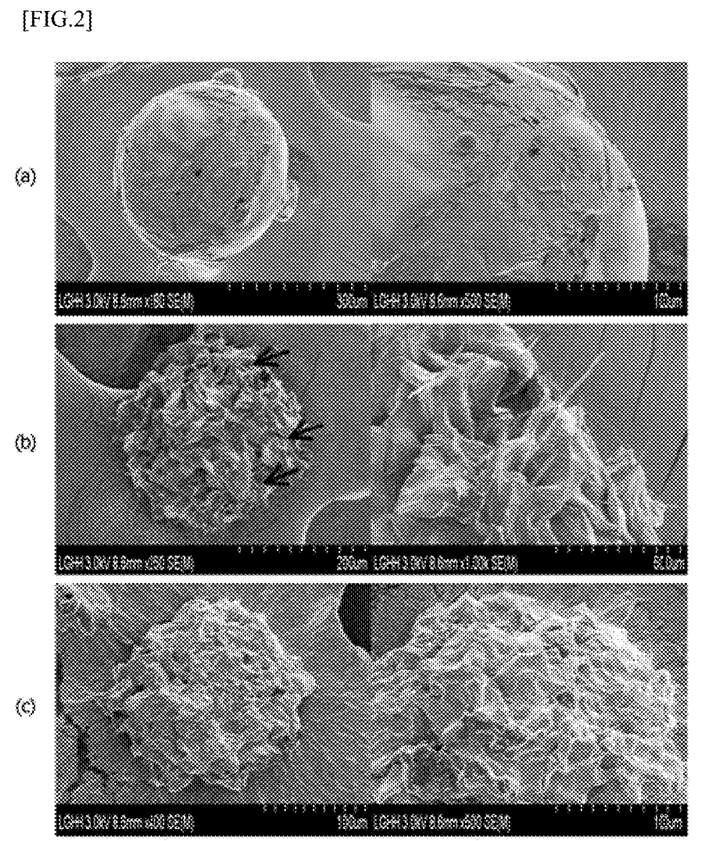

Referring to FIGS. 1 and 2, it can be seen that the particles not containing a ceramide (FIGS. 1A and 2A) and the particles containing a ceramide and typical lipids (FIGS. 1B and 2B) were in the form of a general lipid capsule with a monolayer structure, in which hydrophobic ingredients were simply agglomerated. In addition, in the case of Comparative Example 2, it can be seen that a wax was precipitated in the particle surface as shown in FIG. 2B.

On the other hand, it can be seen that the particles containing a ceramide and phytosphingosine (FIGS. 1C and 2C) had a specific structure in which the outer surface of particles was differentiated as a shell unlike the above-described two cases and showed no precipitation of a ceramide despite a high content of ceramide as shown in FIG. 2C.

2) Confirmation of Skin Hydration Improvement Effect

Figure 3:
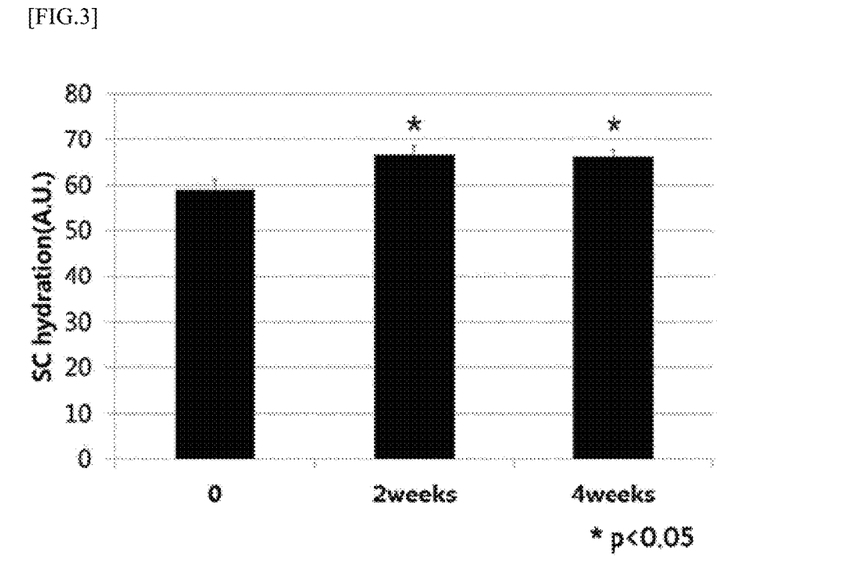
FIG. 3 is a graph illustrating the skin moisture content after application of a cosmetic composition including particles prepared according to the present invention onto the skin for 4 weeks (n=22, *p<0.05).

The cosmetic composition of Example 1 was applied onto the skin for 4 weeks, and skin hydration was measured (FIG. 3).

All 22 subjects who completed this measurement were female with an average age of 47.182 years. The selected subjects had no specific skin symptoms and also had no medical history or drug history that could affect the test.

For the instrument evaluation, the subjects were stabilized in a waiting room at a constant temperature and humidity of 20 to 25° C. and 40 to 60% for 30 minutes to adapt their skin surface temperatures and humidities to the environment of the measurement space, and water intake was restricted during the stabilization. For objective measurement, one researcher conducted the measurement, and the same site was measured for each measurement.

The skin hydration measurement was conducted by measuring the same site of the face before and after the application of the test composition using Corneometer CM 825 (Courage+Khazaka Electronic GmbH, Germany). The measurement was conducted three times through a sensor by allowing a Corneometer probe to be brought into contact with the skin, and an average value thereof was used as the data for evaluating skin hydration. The unit is expressed by the unit constant A.U., and an increase in measurement value indicates an increase in skin hydration.

As a result, it can be seen that the skin hydration was increased by about 7.93% after 2-week application of the cosmetic composition according to the present invention and increased by about 7.23% after 4-week application compared to that before the application. Therefore, the cosmetic composition according to the present invention was confirmed to help to improve skin hydration.

Examples 2 and 3 and Comparative Example 3.
Preparation of Cosmetic Composition According to Ceramide Content In order to confirm transepidermal water loss (TEWL) according to a ceramide content, cosmetic compositions were prepared in compositions shown in the following Table 2. In this case, cosmetic compositions were prepared in the same manner as in Example 1 except for a ceramide content.

TABLE 2

| | Ingredient (parts by weight) | Comparative Example 3 | Example 2 | Example 3 |
|---|---|---|---|---|
| Aqueous phase part | Purified water | 75.8 | 74.8 | 69.8 |
| | Acrylate/C10-30 alkyl acrylate crosspolymer | 0.2 | 0.2 | 0.2 |
| | Glycerin | 5 | 5 | 5 |
| | Dipropylene glycol | 5 | 5 | 5 |
| | 1,2-Hexanediol | 2 | 2 | 2 |
| Oil-phase part | Caprylic/capric triglyceride | 2.4 | 2.4 | 2.4 |
| | Behenic acid | 3.6 | 3.6 | 3.6 |
| | Behenyl alcohol | 2.4 | 2.4 | 2.4 |
| | Cholesterol | 3 | 3 | 3 |
| | Phytosphingosine | 0.6 | 0.6 | 0.6 |
| | Ceramide NP | 0 | 1 | 6 |
| | Total | 100 | 100 | 100 |

Experimental Example 2. Confirmation of Skin Barrier Recovery Rate

The cosmetic composition was applied onto a damaged skin model for 3 days while varying a ceramide content, and TEWL was measured to confirm a skin barrier recovery rate.

All 5 subjects of this experiment were female with an average age of 29.2 years. The selected subjects had no specific skin symptoms and also had no medical history or drug history that could affect the test.

In this test, a 1% SLS patch was attached to the left forearm of the subject to induce skin irritation. The same researcher induced skin irritation for 24 hours by attaching a patch to the designated test site, then evaluated the presence or absence of skin irritation, and conducted instrument measurement for a site to which the test composition was applied and a site to which it was not applied.

For the instrument evaluation, the subjects were stabilized in a waiting room at a constant temperature and humidity of 20 to 25° C. and 40 to 60% for 30 minutes to adapt their skin surface temperatures and humidities to the environment of the measurement space, and water intake was restricted during the stabilization. For objective measurement, one researcher conducted the measurement, and the same site was measured for each measurement.

The TEWL measurement was conducted by measuring the same site of the forearm before and after the application of the test composition using Tewameter TM300 (Cutometer® MPA 580, Courage+Khazaka Electronic GmbH, Germany). The same researcher measured TEWL by allowing a probe to be brought into contact with the forearm of all test subjects with the same pressure. The measurement was conducted three times through a sensor by allowing a Tewameter probe to be brought into contact with the skin, and an average value thereof was used as the data for evaluating a skin barrier recovery rate. The skin barrier recovery rate was calculated by the following equation, and a higher skin barrier recovery rate indicates that TEWL is improved by the test composition, which helps in skin barrier recovery.

Skin barrier recovery rate (%)=(TEWL after induction of skin irritation−TEWL at the time of measurement)/(TEWL after induction of skin irritation−TEWL before induction of skin irritation)×100

Figure 4:
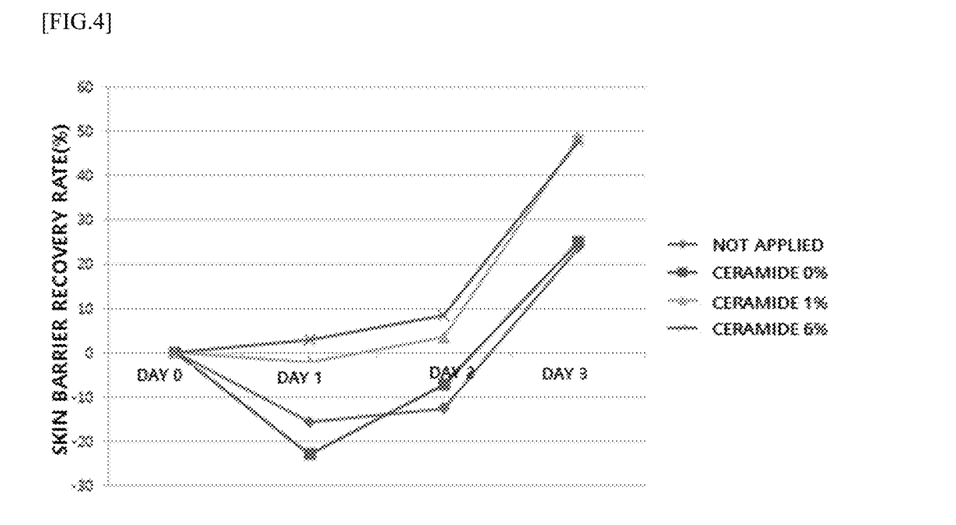
FIG. 4 is a graph illustrating the skin barrier recovery rate of a cosmetic composition including ceramide particles according to the present invention according to a ceramide content.

The skin barrier recovery rate calculated using TEWL after application of the composition onto the skin is graphically shown in FIG. 4.

As shown in FIG. 4, it can be seen that the cosmetic composition of Example 3, which contained 6 parts by weight of a ceramide, showed the highest skin barrier recovery on day 1, and the cosmetic compositions containing a ceramide showed further recovered skin barriers on day 3 ($p<0.05$). From this result, it was confirmed that the particles according to the present invention can achieve desired effects while containing a high content of ceramide.

Experimental Example 3. Confirmation of Formulation Stability

The compositions prepared in Example 1 and Comparative Examples 1 and 2 were stored at varying temperatures for a long period of time, and the formulation stability thereof was confirmed. The compositions were stored at 25° C., 0° C., and 45° C. and also stored in a chamber whose temperature circulates from 0° C. to 45° C., and formulation stability against temperature change was confirmed. Results thereof are shown in the following Table 3.

TABLE 3

| Condition | | Example 1 | Comparative Example 1 | Comparative Example 2 |
|---|---|---|---|---|
| 25° C. | 1 week | Good | Good | Good |
| | 4 weeks | Good | Good | Precipitated in needle shape |
| | 8 weeks | Good | Good | Precipitated in needle shape |
| | 16 weeks | Good | Good | Precipitated in needle shape |

TABLE 3-continued

| Condition | | Example 1 | Comparative Example 1 | Comparative Example 2 |
|---|---|---|---|---|
| 0° C. | 1 week | Good | Good | Good |
| | 4 weeks | Good | Good | Good |
| | 8 weeks | Good | Good | Good |
| | 16 weeks | Good | Good | Good |
| 45° C. | 1 week | Good | Coagulated | Coagulated and precipitated in needle shape |
| | 4 weeks | Good | Coagulated | Coagulated and precipitated in needle shape |
| | 8 weeks | Good | Coagulated | Coagulated and precipitated in needle shape |
| 0° C.↔45° C. | 1 week | Good | Coagulated | Coagulated and precipitated in needle shape |
| | 4 weeks | Good | Coagulated | Particle surface was cracked |

As shown in Table 3, Comparative Example 1, which was in the form of a general lipid capsule not accommodating a ceramide, showed that particles were agglomerated (coagulated) at 45° C., and Comparative Example 2 showed agglomeration of particles, precipitation of the inner material of particles, or cracking in the particle surface at all temperatures except for 0° C. On the other hand, Example 1 of the present invention showed that particles were stably present at all temperatures.

Examples 4 to 6. Preparation of Cosmetic Composition Including Particles Containing High Content of Ceramide In order to confirm that the above-prepared cosmetic composition including particles containing a high content of ceramide is applicable regardless of viscosity, cosmetic compositions were prepared in compositions shown in the following Table 4. Specifically, cosmetic compositions of Examples 4 to 6 were prepared as follows. First, an aqueous phase part was introduced into a gum mixer and uniformly dispersed, ceramide particles finally separated from the cosmetic composition prepared in Example 2 were added, and stirring was performed for 5 minutes, thereby preparing a cosmetic composition.

TABLE 4

| | Ingredient (parts by weight) | Example 4 | Example 5 | Example 6 |
|---|---|---|---|---|
| Aqueous phase part | Purified water | 77.7 | 77.08 | 76.74 |
| | Acrylate/C10-30 alkyl acrylate crosspolymer | 0.15 | — | — |
| | Carbomer | — | 0.46 | 0.3 |
| | Glyceryl acrylate/acrylic acid copolymer | — | — | 0.4 |
| | Ammonium acryloyldimethyltaurate/VP copolymer | — | — | 0.3 |
| | Trisodium EDTA | 0.02 | 0.02 | 0.02 |
| | Glycerin | 10 | 10 | 10 |
| | 1,2-Hexanediol | 2 | 2 | 2 |
| | Tromethamine | 0.13 | 0.44 | 0.24 |

TABLE 4-continued

| Ingredient (parts by weight) | | Example 4 | Example 5 | Example 6 |
|---|---|---|---|---|
| Addition part | Ceramide particle-containing cosmetic composition (Example 2) | 10 | 10 | 10 |
| | Total | 100 | 100 | 100 |

Experimental Example 4. Confirmation of Formulation Stability

The compositions prepared in Examples 4 to 6 were stored at varying temperatures for a long period of time, and the formulation stability thereof was confirmed. The compositions were stored at 25° C., 0° C., and 45° C. and also stored in a chamber whose temperature circulates from 0° C. to 45° C., and formulation stability against temperature change was confirmed. The viscosity was measured at 25° C. using a Brookfield viscometer (spindle #4, 30 rpm) after preparation, and results thereof are shown in the following Table 5.

TABLE 5

| | | Example 4 | Example 5 | Example 6 |
|---|---|---|---|---|
| Viscosity (cps) | | 540 | 14,800 | Not measurable |
| Phase | | Liquid | Lotion | Cream |
| 25° C. | 1 week | Good | Good | Good |
| | 4 weeks | Good | Good | Good |
| | 8 weeks | Good | Good | Good |
| | 16 weeks | Good | Good | Good |
| 0° C. | 1 week | Good | Good | Good |
| | 4 weeks | Good | Good | Good |
| | 8 weeks | Good | Good | Good |
| | 16 weeks | Good | Good | Good |
| 45° C. | 1 week | Good | Good | Good |
| | 4 weeks | Good | Good | Good |
| | 8 weeks | Good | Good | Good |
| | 16 weeks | Good | Good | Good |
| 0° C.↔45° C. | 1 week | Good | Good | Good |
| | 4 weeks | Good | Good | Good |

As a result, the viscosity of Example 6 exceeded 20,000 cps when measured using the same measurement standards as in Examples 4 and 5, so the measurement thereof was impossible. From this experiment, it was confirmed that the compositions of Examples 4 to 6 included well-dispersed ceramide particles and had no problem in stability regardless of viscosity.

The invention claimed is:

1. A method of preparing a cosmetic composition comprising ceramide-accommodating particles, comprising:
   preparing ceramide-accommodating particles by mixing an oil-phase part comprising a ceramide and phytosphingosine with an aqueous phase part,
   wherein in the step of mixing, the oil-phase part is dispersed in the aqueous phase part by permeating the oil-phase part through an emulsification membrane to prepare the ceramide-accommodating particles,
   wherein the oil-phase part is included at 20 parts by weight or less with respect to 100 parts by weight of the entire composition,
   wherein the particles have a membrane with a multi-layered lamellar structure and a core accommodating the ceramide, and
   wherein the particles have an outer coating membrane formed of phytosphingosine,
   wherein the aqueous phase part either comprises purified water and tromethamine, or consists of purified water, C10-C30 alkyl acrylate crosspolymer, glycerin, dipropylene glycol, and 1,2-hexanediol, and
   wherein the ceramide is one or more selected from the group consisting of ceramide EOP, ceramide NS, ceramide NP, ceramide AS, ceramide EOS, ceramide AP, ceramide NDS, glucosylceramide, and omega-hydroxyceramide.

2. The method of claim 1, wherein the particles have an average particle diameter of 50 to 300 μm.

3. The method of claim 1, wherein the ceramide is included at 10 to 50 wt % per particle.

4. The method of claim 1, wherein the ceramide is included at 0.001 to 10 parts by weight with respect to 100 parts by weight of the entire composition.

5. The method of claim 1, wherein the phytosphingosine is included at 0.001 to 5 parts by weight with respect to 100 parts by weight of the entire composition.

6. The method of claim 1, wherein the cosmetic composition is in an oil-in-water (O/W) formulation.

7. The method of claim 1, wherein the oil-phase part further comprises one or more oil-phase ingredients selected from the group consisting of cholesterol, a neutral lipid, a fatty acid, a fatty alcohol, an oil, and a wax.

8. The method of claim 7, wherein the oil is one or more selected from the group consisting of a silicone-based wax, an ester-based oil, a hydrocarbon-based oil, and a vegetable oil.

9. The method of claim 7, wherein the wax is one or more selected from the group consisting of a hydrocarbon-based wax, a vegetable wax, and a silicone wax.

10. The method of claim 1, wherein the cosmetic composition has a viscosity of 0.1 to 40,000 cps.

11. The method of claim 1, wherein the oil-phase part is permeated through the emulsification membrane under a pressure condition of 0.1 to 100 kPa.

* * * * *